United States Patent
Li et al.

(10) Patent No.: US 11,612,643 B2
(45) Date of Patent: Mar. 28, 2023

(54) COL14A1-DERIVED TUMOR ANTIGEN POLYPEPTIDE AND USE THEREOF

(71) Applicant: Genoimmune Therapeutics Co., Ltd., Hubei (CN)

(72) Inventors: Bo Li, Guangdong (CN); Geng Liu, Guangdong (CN); Si Qiu, Guangdong (CN); Dongli Li, Guangdong (CN); Chongming Jiang, Guangdong (CN); Shuntao Luo, Guangdong (CN); Xiumei Lin, Guangdong (CN); Ting An, Guangdong (CN); Yong Hou, Guangdong (CN); Chengchi Chao, Guangdong (CN); Zhen Cheng, Guangdong (CN); Handong Li, Guangdong (CN); Naibo Yang, Guangdong (CN)

(73) Assignee: GENOIMMUNE THERAPEUTICS CO., , LTD., Wuhan (CN)

( * ) Notice: Subject to any disclaimer, the term of this patent is extended or adjusted under 35 U.S.C. 154(b) by 675 days.

(21) Appl. No.: 16/338,201

(22) PCT Filed: Sep. 30, 2016

(86) PCT No.: PCT/CN2016/100979
§ 371 (c)(1),
(2) Date: Mar. 29, 2019

(87) PCT Pub. No.: WO2018/058490
PCT Pub. Date: Apr. 5, 2018

(65) Prior Publication Data
US 2019/0224291 A1    Jul. 25, 2019

(51) Int. Cl.
| | | |
|---|---|---|
| *A61K 39/00* | (2006.01) | |
| *C07K 7/06* | (2006.01) | |
| *C07K 14/78* | (2006.01) | |
| *A61P 35/00* | (2006.01) | |
| *C07K 16/32* | (2006.01) | |
| *C07K 14/47* | (2006.01) | |
| *G01N 33/574* | (2006.01) | |

(52) U.S. Cl.
CPC .......... *A61K 39/0011* (2013.01); *A61P 35/00* (2018.01); *C07K 7/06* (2013.01); *C07K 14/4748* (2013.01); *C07K 14/78* (2013.01); *C07K 16/32* (2013.01); *G01N 33/57484* (2013.01); *A61K 2039/5154* (2013.01); *C07K 2317/34* (2013.01)

(58) Field of Classification Search
CPC ..... A61K 2039/5154; G01N 33/57484; C07K 14/78; C07K 7/06; C07K 7/08; C07K 9/00; C07K 14/00; A61P 35/00
See application file for complete search history.

(56) References Cited

FOREIGN PATENT DOCUMENTS

| | | | |
|---|---|---|---|
| CN | 101107367 A | 1/2008 | |
| CN | 101273144 A | 9/2008 | |
| CN | 103570818 A | 2/2014 | |
| WO | 2013090811 A1 | 6/2013 | |
| WO | WO-2015018805 A1 * | 2/2015 | ............. A61K 35/17 |
| WO | 2015149721 A1 | 10/2015 | |
| WO | WO-2016062659 A1 * | 4/2016 | ........... C12Q 1/6886 |
| WO | WO-2018045509 A1 * | 3/2018 | ....... G01N 33/57492 |

OTHER PUBLICATIONS

Knutson et al. (J Clin Invest. 2001; 107(4):477-484) (Year: 2001).*
Cazares et al. (Clinical Cancer Research, 2009, vol. 15, pp. 5541-5551 (Year: 2009).*
Wissinger, E., "CD8+ T Cells" (2013), downloaded Mar. 11, 2021, from https://www.immunology.org/public-information/bitesized-immunology/cells/cd8-t-cells (Year: 2013).*
Neidert et al. Acta neuropathologica, 2018, 135(6), 923-938 (Year: 2018).*
Patent Translation of WO2018/045509, May 11, 2021 (Year: 2021).*
Int'l Search Report dated Jun. 7, 2017 in Int'l Application No. PCT/CN2016/100979.
Knutson et al., "Immunization with a HER-2/neu helper peptide vaccine generates HER-2/neu CD8 T-cell immunity in cancer patients," J. Clin. Invest., vol. 107, No. 4, pp. 477-484 (2001).
Office Action dated Jun. 28, 2022 in CN Application No. 201680089718.X.

* cited by examiner

*Primary Examiner* — Karen A. Canella
(74) *Attorney, Agent, or Firm* — Panitch Schwarze Belisario & Nadel LLP; Stephany G. Small; Lars. H. Genieser

(57) ABSTRACT

Provided are a tumour antigen polypeptide having the amino acid sequence as shown in SEQ ID NO: 2 or a variant thereof; a nucleic acid encoding same; a nucleic acid construct, an expression vector, and a host cell comprising the encoding nucleic acid; and an antigen presenting cell presenting the tumour antigen polypeptide on the cell surface and an immune effector cell thereof. Also provided is the use of the polypeptide, nucleic acid, antigen presenting cell or immune effector cell in the diagnosis, prevention and treatment of cancers.

8 Claims, 6 Drawing Sheets
Specification includes a Sequence Listing.

SEQUENCE LISTING

```
<160> NUMBER OF SEQ ID NOS: 14

<210> SEQ ID NO 1
<211> LENGTH: 9
<212> TYPE: PRT
<213> ORGANISM: human

<400> SEQUENCE: 1

Phe Met Val Asp Gly Ser Trp Ser Ile
1               5
```

<210> SEQ ID NO 2
<211> LENGTH: 9
<212> TYPE: PRT
<213> ORGANISM: artificial sequence
<220> FEATURE:
<223> OTHER INFORMATION: the mutant COL14A1 peptide of the present
      application

<400> SEQUENCE: 2

Phe Met Val Asp Gly Phe Trp Ser Ile
1               5

<210> SEQ ID NO 3
<211> LENGTH: 9
<212> TYPE: PRT
<213> ORGANISM: artificial sequence
<220> FEATURE:
<223> OTHER INFORMATION: the variant of the mutant COL14A1 peptide of
      the present application

<400> SEQUENCE: 3

Phe Met Val Asp Gly Phe Trp Ser Leu
1               5

<210> SEQ ID NO 4
<211> LENGTH: 9
<212> TYPE: PRT
<213> ORGANISM: artificial sequence
<220> FEATURE:
<223> OTHER INFORMATION: the variant of the mutant COL14A1 peptide of
      the present application

<400> SEQUENCE: 4

Phe Met Val Asp Gly Phe Trp Ser Val
1               5

<210> SEQ ID NO 5
<211> LENGTH: 9
<212> TYPE: PRT
<213> ORGANISM: artificial sequence
<220> FEATURE:
<223> OTHER INFORMATION: the variant of the mutant COL14A1 peptide of
      the present application

<400> SEQUENCE: 5

Phe Leu Val Asp Gly Phe Trp Ser Ile
1               5

<210> SEQ ID NO 6
<211> LENGTH: 9
<212> TYPE: PRT
<213> ORGANISM: artificial sequence
<220> FEATURE:
<223> OTHER INFORMATION: the variant of the mutant COL14A1 peptide of
      the present application

<400> SEQUENCE: 6

Phe Leu Val Asp Gly Phe Trp Ser Leu
1               5

<210> SEQ ID NO 7
<211> LENGTH: 9
<212> TYPE: PRT
<213> ORGANISM: artificial sequence
<220> FEATURE:
<223> OTHER INFORMATION: the variant of the mutant COL14A1 peptide of
      the present application

```
<400> SEQUENCE: 7

Phe Leu Val Asp Gly Phe Trp Ser Val
1               5

<210> SEQ ID NO 8
<211> LENGTH: 27
<212> TYPE: DNA
<213> ORGANISM: artificial sequence
<220> FEATURE:
<223> OTHER INFORMATION: the nucleotide sequence encoding the wild-type
      COL14A1 peptide

<400> SEQUENCE: 8
ttcatggtgg atggatcttg gagcata                                          27

<210> SEQ ID NO 9
<211> LENGTH: 27
<212> TYPE: DNA
<213> ORGANISM: artificial sequence
<220> FEATURE:
<223> OTHER INFORMATION: the nucleotide sequence encoding the mutant
      COL14A1 peptide of the present application

<400> SEQUENCE: 9
ttcatggtgg atggattctg gagcata                                          27

<210> SEQ ID NO 10
<211> LENGTH: 27
<212> TYPE: DNA
<213> ORGANISM: artificial sequence
<220> FEATURE:
<223> OTHER INFORMATION: the nucleotide sequence encoding the variant of
      the mutant COL14A1 peptide of the present application

<400> SEQUENCE: 10
ttcatggtgg atggattctg gagcctg                                          27

<210> SEQ ID NO 11
<211> LENGTH: 27
<212> TYPE: DNA
<213> ORGANISM: artificial sequence
<220> FEATURE:
<223> OTHER INFORMATION: the nucleotide sequence encoding the variant of
      the mutant COL14A1 peptide of the present application

<400> SEQUENCE: 11
ttcatggtgg atggattctg gagcgtc                                          27

<210> SEQ ID NO 12
<211> LENGTH: 27
<212> TYPE: DNA
<213> ORGANISM: artificial sequence
<220> FEATURE:
<223> OTHER INFORMATION: the nucleotide sequence encoding the variant of
      the mutant COL14A1 peptide of the present application

<400> SEQUENCE: 12
ttcctggtgg atggattctg gagcata                                          27

<210> SEQ ID NO 13
<211> LENGTH: 27
<212> TYPE: DNA
<213> ORGANISM: artificial sequence
<220> FEATURE:
<223> OTHER INFORMATION: the nucleotide sequence encoding the variant of
      the mutant COL14A1 peptide of the present application
```

```
<400> SEQUENCE: 13
ttcctggtgg atggattctg gagcctg                                              27

<210> SEQ ID NO 14
<211> LENGTH: 27
<212> TYPE: DNA
<213> ORGANISM: artificial sequence
<220> FEATURE:
<223> OTHER INFORMATION: the nucleotide sequence encoding the variant of
      the mutant COL14A1 peptide of the present application

<400> SEQUENCE: 14
ttcctggtgg atggattctg gagcgtc                                              27
```

COL14A1-DERIVED TUMOR ANTIGEN POLYPEPTIDE AND USE THEREOF

CROSS-REFERENCE TO RELATED APPLICATION

This application is a Section 371 of International Application No. PCT/CN2016/100979, filed Sep. 30, 2016, which was published in the Chinese language on Apr. 5, 2018, under International Publication No. WO 2018/058490 A1, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688287_8US_Sequence Listing", creation date of Mar. 28, 2019, and having a size of about 4 KB. The sequence listing submitted via EFS-Web is part of the specification and is herein incorporated by reference in its entirety.

TECHNICAL FIELD

The present invention relates to the technical field of the diagnosis, prevention and immunotherapy of cancers, and in particular to a tumor antigen peptide resulting from mutation of COL14A1 gene, the related products thereof, and the medical use thereof.

BACKGROUND

Cancer is a disease in which cell proliferation is out of control due to genetic mutations in cells. At present, it has become a major threat to human health and is one of the main causes of human death. According to the "Global Cancer Report 2014" published by World Health Organization (WHO), cancer patients and death cases were rapidly increased in 2012 worldwide with nearly half of new cancer cases occurred in Asia, most of which occurred in China, and the amount of new cancer cases in China ranks the first in the world[1]. According to data from "Annual Report of Cancer Registration in China in 2012", about 3.5 million new cancer cases every year were reported in China, and about 2.5 million people died therefromm. Therefore, it would be of great clinical value to find a highly effective and specific cancer treatment method.

Traditional treatments for tumor mainly include surgery, radiotherapy and chemotherapy. However, these therapies have serious limitations. For example, the tumor metastasis and recurrence rate after surgical resection is high due to proximal invasion or distant metastasis of cancer cells, and radiotherapy and chemotherapy can cause serious damage to the body's own normal cells, especially hematopoietic system and immune system of the body, and it is therefore difficult for patients who have developed tumor metastasis to achieve better long-term efficacy[3]. With in-depth studies of the molecular mechanism of tumors and further development of biotechnology, targeted drug therapies and immunotherapies play an increasingly important role in the comprehensive treatment of tumors. The targeted therapies mainly include monoclonal antibodies (sometimes classified as passive immunotherapy) and small molecule targeted drugs, and the immunotherapies mainly include cytokine therapy, immune checkpoint monoclonal antibody, adoptive cell transfer and tumor vaccine, etc.[4, 5]. Immunotherapies control and kill tumor cells by activating the immune system of the body and enhancing the anti-tumor immunity of tumor microenvironment, and thus have the advantages of high efficiency and specificity and good tolerance, and have broad prospects in cancer treatment[5, 6].

Vaccines for tumor immunotherapy mainly include tumor cell vaccines, dendritic cell vaccines, protein & peptide vaccines, nucleic acid vaccines, genetic engineering vaccines and anti-idiotype tumor vaccines[7]. The main mechanism of these vaccines in killing a tumor is the initiation of an immune response against tumor-specific antigen in a patient, including antigen-antibody reaction and a CTL-specific killing and the like, among which the CTL-specific killing plays a great role in immune responses to tumors. A tumor-specific peptide is a tumor-specific antigen that primarily causes CTL-specific killing, and includes tumor-specific mutant peptides as well as tumor-specific highly expressed peptides. Wherein, the tumor-specific mutant peptides are only present in tumor tissues of patients and therefore can act as a specific target of tumor immunotherapy, which has the characteristics of good safety and few side effects. Immunotherapies targeting tumor-specific mutant peptides, such as peptide-specific DC-CTL and TIL adoptive transfer, have a good therapeutic effect[8,9].

Tumor-specific peptides can be recognized by CTL or TIL cells by virtue of the antigen presenting function of human leukocyte antigen (HLA). The human leukocyte antigen is mainly divided into two subtypes I and II. Type I HLA is further mainly divided into three subtypes A, B and C, each of which can be further divided into multiple subtypes depending on its sequence. HLA-A0201 is one of the HLA-A subtypes, and occurs in 13% of the Chinese population, which is a high proportion. Different peptides bind to the HLA-A0201 subtype with different binding affinities. In a tumor patient with a specific HLA subtype, due to the specific HLA subtype, only a portion of mutant peptides can bind to the HLA and be presented to CTL or TIL cells by the HLA.

The COL14A1 gene encodes Human Collagen alpha-1 (XIV) chain having a length of 1796 amino acids and a molecular weight of 193,515 daltons. Type XIV collagen binds to the surface of fibrils and participates in the regulation of fibril formation, and is mainly related to the structural composition and collagen binding of extracellular matrix.

REFERENCES

[1] World Health Organization. Globocan 2012: Estimated cancer incidence, mortality and prevalence worldwide in 2012.

[2] Bernard W. Stewart C P W. World Cancer Report 2014. 2014.

[3] Xiaoqin Ha, Shangdi Zhang, Zhihua Yang, Jun Zhang. A new technology for tumor biotherapy—targeted gene therapy. Medicine Journal of Chinese People's Liberation Army 2014; 26:24-7.

[4] Mellman I, Coukos G, Dranoff G. Cancer immunotherapy comes of age. Nature 2011; 480:480-9.

[5] Chen D S, Mellman I. Oncology meets immunology: the cancer-immunity cycle. Immunity 2013; 39:1-10.

[6] Currie G A. Eighty years of immunotherapy: a review of immunological methods used for the treatment of human cancer. British journal of cancer 1972; 26:141-53.

[7] Tingting Li, Hui Li, Xicai Wang. The progress of tumor vaccine in oncotherapy. Journal of Modern Oncology 2013; 21:2351-3

[8] Tran E, Turcotte S, Gros A, et al. Cancer immunotherapy based on mutation-specific CD4+ T cells in a patient with epithelial cancer. Science. 2014. 344(6184): 641-5.

[9] Cobbold M, De La Pena H, Norris A, et al. MHC class I-associated phosphopeptides are the targets of memory-like immunity in leukemia. Sci Transl Med. 2013. 5(203): 203ra125.

SUMMARY OF THE INVENTION

The object of the present invention is to provide a tumor antigen peptide resulting from mutation of the COL14A1 gene, a nucleic acid encoding the tumor antigen peptide, a nucleic acid construct, an expression vector and a host cell comprising the nucleic acid, and an antigen-presenting cell and an immune effector cell of the tumor antigen peptide, and the medical use thereof.

Mutation of the COL14A1 gene causes a change in its amino acid sequence such that the amino acid at position 1040 is mutated from serine to phenylalanine. The mutated COL14A1 gene is expressed at a high level in tumor tissues and, therefore, enables high expression of the related peptide in tumor tissues. So far, the tumor-specific peptide sequence caused by the above mutation of COL14A1 gene has not been reported in China and abroad, nor has the peptide been used in the study of immunotherapy of tumors and in the study of the affinity to HLA-A0201. Since the peptide is expressed only in mutated tumor tissues, it is specific for tumor tissues, thus having important significance for the detection, early prevention and immunotherapy of tumors in patients.

In a first aspect, the present invention provides an isolated peptide selected from the group consisting of:

(a) a peptide consisting of the amino acid sequence shown in SEQ ID NO: 2 (that is, FMVDGFWSI);

(b) a peptide which is derived from the amino acid sequence shown in SEQ ID NO: 2 by substitution, addition and/or deletion of one or more amino acid residues therein, and has the ability to induce cytotoxic T lymphocytes; and (c) a variant or derivative of the peptide (a) or (b) that has the ability to induce cytotoxic T lymphocytes, or an immunologically active fragment thereof.

The inventors of the present invention have found from the breast cancer database that mutation of the COL14A1 gene results in the mutation of the encoded amino acid at position 1040 from serine (Ser, S) to phenylalanine (Phe, F), and have predicted by a computer prediction software that the mutant peptide sequence has a high affinity to HLA-A, especially to HLA-A0201. The peptide consists of 9 amino acids with a molecular weight of 974.23 Daltons and a full length sequence of: FMVDGFWSI (i.e., SEQ ID NO: 2). By chemically synthesizing the peptide and then subjecting the same to an affinity test to T2 cells, it has been confirmed that the peptide does have a high affinity to HLA-A, especially to HLA-A0201. It has been confirmed by in vitro immunogenicity assay (ELISPOT) that the peptide could induce antigen-specific T cells to secrete the cytokine IFN-gamma, and induce an activation reaction of immune cells; and it has been confirmed by LDH-releasing assay that CD8+ T cells could specifically recognize and kill target cells presenting the peptide.

The inventors have also found that the peptide (b) which is derived from the amino acid sequence of the peptide (a) by substitution, addition or deletion of one or more amino acid residues therein may have the above-described functions of the peptide (a), i.e., having a high affinity to HLA-A, especially to HLA-A0201, and able to be specifically recognized by CD8+ T cells, thereby causing a specific immune response; and having an ability to induce cytotoxic T lymphocyte.

Preferably, the substitution, addition and/or deletion of one or more amino acids is the substitution of the amino acid at position 2 and/or position 9 of the amino acid sequence as shown in SEQ ID NO: 2.

More preferably, the substitution, addition and/or deletion of one or more amino acids is the substitution of L for the amino acid at position 2 and/or of L or V for the amino acid at position 9 of the amino acid sequence as shown in SEQ ID NO: 2.

More preferably, the peptide (b) has the amino acid sequence as shown in SEQ ID NO: 3 (i.e., FMVDGFWSL), SEQ ID NO: 4 (i.e., FMVDGFWSV), SEQ ID NO: 5 (i.e., FLVDGFWSI), SEQ ID NO: 6 (i.e., FLVDGFWSL), or SEQ ID NO: 7 (i.e., FLVDGFWSV).

It has been experimentally verified that, compared to the peptide (a), the peptide (b)'s binding affinity to HLA-A, especially to HLA-A0201, is enhanced, but its specificity for T cells is not changed. Thus, both the peptide (b) and the peptide (a) have the same ability to activate a specific T immune.

The peptides of the present invention can be synthesized according to methods used in conventional peptide chemistry, including, for example, the methods described in Peptide Synthesis, Interscience, New York, 1966; and the peptides of the present invention can also be prepared by conventional genetic engineering. For example, conventional DNA synthesis and genetic engineering methods can be used to prepare the peptide by preparing a nucleotide encoding the same, for example by the following procedure: inserting the nucleotide described above into a commonly used expression vector; transforming a host cell with the resulting recombinant expression vector; culturing the resulting transformant; and collecting the peptide from the culture, all of which can be carried out, for example, by referring to the method described in Molecular Cloning, T. Maniatis et al., CSH Laboratory (1983). The peptide obtained by the above method can be verified by reversed-phase high-performance liquid chromatography-mass spectrometry.

In a second aspect, the present invention provides an isolated nucleic acid encoding the isolated peptide as described in the first aspect.

In a third aspect, the present invention provides a nucleic acid construct comprising the nucleic acid as described in the second aspect, and one or more control sequences operably linked thereto and able to direct the production of the peptide in an expression host.

In a fourth aspect, the present invention provides an expression vector comprising the nucleic acid construct as described in the third aspect.

In a fifth aspect, the present invention provides a host cell into which the nucleic acid construct as described in the third aspect or the expression vector as described in the fourth aspect has been transformed or transfected.

In a sixth aspect, the present invention provides an antigen-presenting cell which presents the isolated peptide as described in the first aspect on the cell surface.

In a seventh aspect, the present invention provides a method for producing the antigen-presenting cell as described in the sixth aspect, comprising the step of: contacting the peptide as described in the first aspect with a cell having an antigen-presenting ability, or comprising the steps of: introducing the nucleic acid as described in the second aspect, or the nucleic acid construct as described in the third aspect, or the expression vector as described in the fourth aspect into a cell having an antigen-presenting ability and expressing the same therein.

Preferably, the cell having an antigen-presenting ability is a dendritic cell.

In an eighth aspect, the present invention provides an immune effector cell which can recognize the peptide as described in the first aspect, or recognize an antigen-presenting cell which presents the peptide as described in the first aspect on the cell surface.

In a ninth aspect, the present invention provides a method for producing the immune effector cell as described in the eighth aspect, comprising the step of: contacting the antigen-presenting cell as described in the sixth aspect with a cell with the ability of immune effect.

Preferably, the cell with the ability of immune effect is a T cell, preferably a CD8+ T cell.

In a tenth aspect, the present invention provides a targeted immune cell population which is formed by mixing and co-cultivating antigen-presenting cells with lymphocytes.

In an eleventh aspect, the present invention provides a conjugate comprising the peptide as described in the first aspect and an anti-cancer drug.

In a twelfth aspect, the present invention provides an antibody which can specifically recognize the peptide as described in the first aspect.

In a thirteenth aspect, the present invention provides a method for producing an antibody, comprising:

immunizing an animal with the peptide as described in the first aspect;

collecting serum of the immunized animal; and purifying the antibody of interest from the serum.

In a fourteenth aspect, the present invention provides a vaccine for treating or preventing a cancer in a patient, comprising the peptide as described in the first aspect, or the nucleic acid as described in the second aspect, or the nucleic acid construct as described in the third aspect, or the expression vector as described in the fourth aspect, or the antigen-presenting cell as described in the sixth aspect, or the immune effector cell as described in the eighth aspect.

Preferably, the cancer is a cancer in which the peptide as described in the first aspect is expressed.

More preferably, the cancer is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a fifteenth aspect, the present invention provides a pharmaceutical composition for treating or preventing a cancer in a patient, comprising the peptide as described in the first aspect, and a pharmaceutically acceptable carrier.

In a sixteenth aspect, the present invention provides use of the peptide as described in the first aspect for the preparation of an antibody for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a seventeenth aspect, the present invention provides use of the peptide as described in the first aspect for the preparation of a medicament for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In an eighteenth aspect, the present invention provides use of the peptide as described in the first aspect for the preparation of a vaccine for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a nineteenth aspect, the present invention provides use of a detection reagent for the peptide as described in the first aspect or for the nucleic acid as described in the second aspect for the preparation of a kit for diagnosing a cancer in a patient.

Preferably, the cancer is a cancer in which the peptide as described in the first aspect is expressed.

More preferably, the cancer is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a twentieth aspect, the present invention provides a kit for diagnosing a cancer in a patient, comprising a detection reagent for the peptide as described in the first aspect or for the nucleic acid as described in the second aspect.

In a twenty-first aspect, the present invention provides a therapeutic method, comprising:

administering to a patient an effective amount of the peptide as described in the first aspect, the antigen-presenting cell as described in the sixth aspect, the immune effector cell as described in the eighth aspect, the targeted immune cell population as described in the tenth aspect, the conjugate as described in the eleventh aspect, the antibody as described in the twelfth aspect, the vaccine as described in the fourteenth aspect, or the pharmaceutical composition as described in the fifth aspect.

In a twenty-second aspect, the present invention provides a diagnostic method, comprising:

detecting a biological sample derived from a patient for the presence of the peptide as described in the first aspect; and determining the patient as having a tumor based on the presence of the peptide in the biological sample.

Optionally, the tumor expresses both HLA-A0201 and the peptide.

Optionally, the tumor is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

Beneficial Effects

The tumor antigen peptide FMVDGFWSI according to the present invention is produced from tumor-specific mutation of the COL14A1 gene. It is absent in normal human tissues in which the mutation does not occur, and is present only in the tumor tissue of a patient in which the mutation occurs. Because it is only present in the tumor tissue of a patient and not in the normal tissue, it has a high specificity and causes a highly specific immune response. It can cause a specific immune response against tumors. When used as a tumor vaccine, it is safer, has few side effects and rarely causes serious immune reactions as compared to other tumor peptide vaccines, and is suitable for industrial production because of its simple structure and ease to be artificially synthesized.

The specificity between the variant forms of the peptide described above and T cells does not change due to the enhanced binding affinity to HLA-A0201. Therefore, these variant forms have the same ability to activate a specific T immune as the peptide FMVDGFWSI. Thus, the peptide FMVDGFWSI or the variant forms thereof can be used as a target or a vaccine for use in the biotherapies against tumors that express both HLA-A0201 and the mutant peptide. The peptide FMVDGFWSI or the variant forms thereof can be used for the prevention and treatment of tumors by means of peptide+adjuvant, or a peptide-loaded DC vaccine, or a peptide-specific DC-CTL, a DC-CIK vaccine, etc. The tumors include a variety of cancers which express the peptide sequence, such as lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, brain tumors, and the like.

Furthermore, since the peptide of the present invention is present only in tumor tissues, and the presence of the free peptide in serum can be detected by mass spectrometry, it can be used as a tumor marker for the diagnosis of a tumor.

DESCRIPTION OF THE DRAWINGS

FIG. 3 shows the inhibitory effect on tumor growth and mouse survival rate after immunotherapy with the peptide of the present invention; wherein FIG. 3A shows the inhibitory effect on tumor growth after treatment with an adjuvant, an adjuvant+a wild-type peptide (FMVDGSWSI, SEQ ID NO: 1), or an adjuvant+a mutant peptide FMVDGFWSI or the variant peptides thereof, FIG. 3B shows the mouse survival rate after treatment with an adjuvant, an adjuvant+a wild-type peptide (FMVDGSWSI), or an adjuvant+a mutant peptide FMVDGFWSI or the variant peptides thereof.

FIG. 4 shows the inhibitory effect on tumor growth and mouse survival rate after immunotherapy with the peptide of the present invention; wherein FIG. 4A shows the inhibitory effect on tumor growth after treatment with DC loaded with a wild-type peptide (FMVDGSWSI), or DC loaded with a mutant peptide (FMVDGFWSI) or the variant peptides thereof, FIG. 4B shows the mouse survival rate after treatment with DC loaded with a wild-type peptide (FMVDGSWSI), or DC loaded with a mutant peptide FMVDGFWSI or the variant peptides thereof.

FIG. 5 shows the inhibitory effect on tumor growth and mouse survival rate after immunotherapy with the peptide of the present invention; wherein FIG. 5A shows the inhibitory effect on tumor growth after treatment with DCs infected with lentivirus vector carrying a wild-type peptide (FMVDGSWSI), or a mutant peptide (FMVDGFWSI) or the variant peptides thereof; FIG. 5B shows the mouse survival rate after treatment with DCs infected with lentivirus vector carrying a wild-type peptide (FMVDGSWSI), or a mutant peptide (FMVDGFWSI) or the variant peptides thereof.

FIG. 6 shows the inhibitory effect on tumor growth and mouse survival rate after immunotherapy with the peptide of the present invention; wherein FIG. 6A shows the inhibitory effect on tumor growth after treatment with DC loaded with a wild-type peptide (FMVDGSWSI)+CTL, or DC loaded with a mutant peptide (FMVDGFWSI) or the variant peptides thereof+CTL, FIG. 6B shows the mouse survival rate after treatment with DC loaded with a wild-type peptide (FMVDGSWSI)+CTL, or DC loaded with a mutant peptide (FMVDGFWSI) or the variant peptides thereof+CTL.

DETAILED DESCRIPTION

Figure 1:
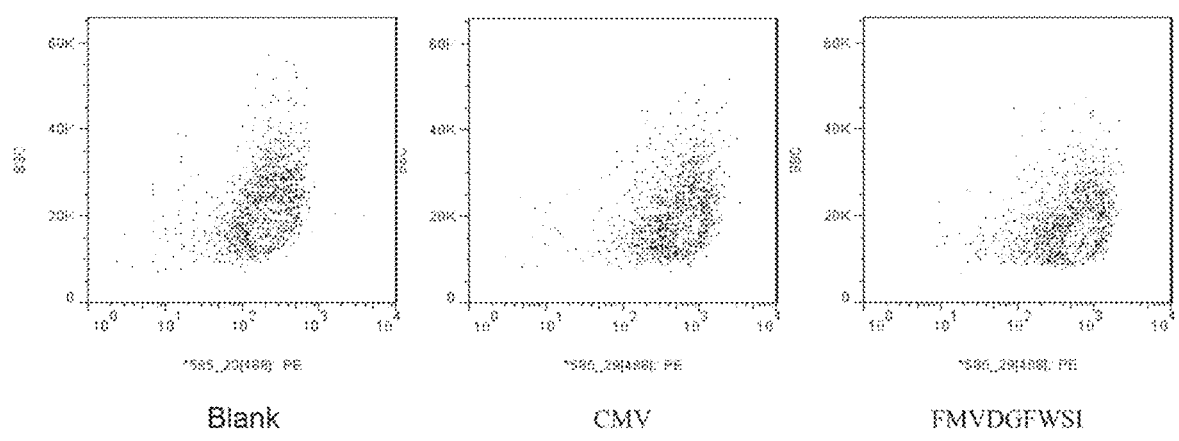
FIG. 1 is a graph showing the results of detecting the affinity of the peptide of the present invention to T2 cells by flow cytometry.

In order to facilitate understanding of the present invention, the following examples are exemplified in the present invention. It should be understood by those skilled in the art that the examples are only to facilitate the understanding of the present invention and should not be construed as specific limitations to the present invention.

Example 1 Affinity Prediction of the Peptides of the Present Invention

Affinity of the peptides was predicted by the following procedure:

Based on the selected HLA allele type, affinity of the peptides was predicted by using a self-developed "software for predicting the binding ability of a mutant peptide based on tumor DNA and RNA sequencing" (software copyright number: 2016SR002835). The prediction results were expressed as IC50 score. An IC50 of less than 500 nm indicated that the peptide had an affinity, and an IC50 of less than 50 nm indicated that the peptide had a high affinity.

The wild-type peptide FMVDGSWSI (SEQ ID NO: 1), the mutant peptide FMVDGFWSI of the present invention and the five variant peptides of the mutant peptide FMVDGFWSI (also belonging to the present invention) were obtained by standard solid phase synthesis and purified by reverse phase HPLC. The purity (>90%) and identity of the peptide were determined by HPLC and mass spectrometry, respectively. This example predicted the affinity of the above peptides of the present invention and the wild-type peptide to HLA-A0201 in the manner as above, and the prediction scores were shown in Table 1 below.

TABLE 1

Affinity prediction results of the peptides to HLA-A0201

| Mutant Peptides | IC50 (nM) | Wild-type Peptide | IC50 (nM) |
| --- | --- | --- | --- |
| FMVDGFWSI | 2.18 | FMVDGSWSI | 3.93 |
| FMVDGFWSL | 2.32 | — | — |
| FMVDGFWSV | 2.56 | — | — |
| FLVDGFWSI | 2.87 | — | — |
| FLVDGFWSL | 3.01 | — | — |
| FLVDGFWSV | 3.14 | — | — |

It can be seen from Table 1 that as predicted by the computer software, the IC50 scores of the mutant peptides of the present invention were less than 50 nM, indicating that the mutant peptides of the present invention had a high affinity to HLA-A0201.

Example 2 Affinity Verification of the Peptides of the Present Invention to T2 Cells According to the manner described in Example 1, the wild-type peptide FMVDGSWSI, the peptide FMVDGFWSI of the present invention and the FMVDGFWSI's five variant peptides were obtained; 2×10⁵ T2 cells (a lymphocyte, tumor cell line, expressing HLA-A0201; T2 cell is a cell strain that is deficient in an antigen peptide transporter (TAP) that is essential for endogenous antigen presentation pathway, and is a hybridoma cell from HLA-A2-positive T and B lymphocytess, and can be used to study the affinity of a peptide to HLA-A2 and the interaction of T cells with MHC-I molecule; ATCC Cat. No.: CRL-1992™) were resuspended into a 24-well plate with 500 μl of serum-free IMDM medium. 10 μg/ml of each peptide as described above was added, and human β2 microglobulin (at a final concentration of 3 μg/ml) was added and cultured overnight in an incubator (37° C., 5% $CO_2$). Two replicate wells were set up for each group. T2 cells without the addition of a peptide were used as a background control (i.e., blank), and the group added with the CMV peptide (NLVPMVATV) was used as a positive control.

Cells were collected by centrifugation of the cell culture at 200 g for 5 minutes. The collected cells were washed twice with PBS, and then directly incubated with FITC-conjugated anti-HLA-A0201 monoclonal antibody at 4° C. for 30 minutes. The mean fluorescence intensity (MFI) was then detected and analyzed by flow cytometer (BD FACSJazz™) and its software. The fluorescence index (FI) was calculated by using the following formula:

$$FI = [MFI_{sample} - MFI_{background}] / MFI_{background};$$

Wherein, the $MFI_{background}$ represents a value without peptide; FI>1.5 indicates that the peptide has a high affinity for HLA-A0201 molecule, 1.0<FI<1.5 indicates that the peptide has a medium affinity for HLA-A0201 molecule, and 0.5<FI<1.0 indicates that the peptide has a low affinity for HLA-A0201 molecule.

The affinity detection results of the respective peptides described above to HLA-A 0201 were shown in Table 2 below.

TABLE 2

| Sample | Concentration of the added peptide | Average fluorescence intensity | FI |
|---|---|---|---|
| FMVDGSWSI | 100 μM | 772.5 | 2.38 |
| FMVDGFWSI | 100 μM | 763.9 | 2.35 |
| FMVDGFWSL | 100 μM | 748.3 | 2.28 |
| FMVDGFWSV | 100 μM | 721.2 | 2.16 |
| FLVDGFWSI | 100 μM | 701.3 | 2.07 |
| FLVDGFWSL | 100 μM | 663.9 | 1.91 |
| FLVDGFWSV | 100 μM | 642.5 | 1.81 |
| blank | 0 μM | 228.3 | 0 |
| CMV | 100 μM | 663.2 | 1.90 |

It can be seen from Table 2 that, through the affinity verification, the FI of the blank group was 0, and the FI of the CMV peptide which was used as a positive control was 1.90, both of which were normal; while the FIs of the wild-type peptide and the mutant peptides of the present invention were both greater than 1.5, further demonstrating that the wild-type peptide and the mutant peptides of the present invention were all highly affinitive.

Example 3 In Vitro Stimulation and Expansion of CD8+ T Cells by the Peptides of the Present Invention $2 \times 10^7$ PBMC cells were taken from the subtype HLA-A0201-positive volunteers. Mononuclear cells were isolated by an adherence method (adhering for 3 h), and CD8+ T cells were isolated by using CD8 magnetic beads. Adherent mononuclear cells were induced into immature DCs with GM-CSF (1000 U/ml) and IL-4 (1000 U/ml), and further induced into peptide-specific mature DCs with IFN-γ (100 U/ml), CD40L (100 U/ml) and each of the mutant peptide FMVDGFWSI of the present invention and the five variant peptides thereof. The mature DCs loaded with peptides were irradiated, and co-cultured with CD8+ T cells from volunteers, and IL-21 was added. After 3 days, IL-2 and IL-7 were supplemented. Afterwards, IL-2 and IL-7 were again supplemented on day 5 and day 7, respectively (the final concentrations of IL-21, IL-2 and IL-7 were 30 ng/ml, 5 ng/ml and 10 ng/ml, respectively). The co-cultured cells were counted on day 10 and subsequently subjected to ELISPOTs and LDH tests. The counting results were shown in Table 3 below.

TABLE 3

Cell counting results after culture

| | Total number of cells in the well before culture | Total number of cells in the well after culture |
|---|---|---|
| FMVDGFWSI | $2.5 \times 10^6$ | $1.72 \times 10^7$ |
| FMVDGFWSL | $2.5 \times 10^6$ | $1.67 \times 10^7$ |
| FMVDGFWSV | $2.5 \times 10^6$ | $1.61 \times 10^7$ |
| FLVDGFWSI | $2.5 \times 10^6$ | $1.56 \times 10^7$ |
| FLVDGFWSL | $2.5 \times 10^6$ | $1.46 \times 10^7$ |
| FLVDGFWSV | $2.5 \times 10^6$ | $1.37 \times 10^7$ |

It can be seen from Table 3 that after 10 days of culture, the cells proliferated significantly, and the expansion fold of the total number of cells was between 5-7 folds, indicating that the addition of the peptides of the present invention can significantly stimulate the expansion of CD8+ T cells.

Example 4 Activation of a CD8+ T Cell Immune Response by the Peptides of the Present Invention as Verified by ELISPOTs In this example, a ELISPOTs detection kit (Cat. No.: 3420-4AST-10, MABTECH) was used to verify the activation of an immune response of CD8+ T cells by the peptides of the present invention.

Principle of the ELISPOTs detection method is as follows: CD8+ T cells can specifically recognize the complex of HLA-A0201 and a peptide. The population of T cells recognizing the complex of the peptide and HLA-A0201 is varying, depending on the peptide sequence. Since T2 cells express HLA-A0201, CD8+ T cells can specifically recognize the T2 cells loaded with a peptide. After specific recognition of the complex of HLA-A0201 and the peptide, peptide-specific CD8+ T cells can be activated again to secrete IFN-gamma interferon. The IFN-gamma interferon secreted by the activated CD8+ T cells can be captured by antibodies on the ELISPOTs plate. Finally, the enzyme-conjugated antibody that recognizes IFN-gamma can degrade the substrate through the enzyme conjugated thereto and develop color, eventually producing spots. The number of spots represents the number of cells that are activated to secrete IFN-gamma interferon.

The cultured cells from Example 3 were added, along with T2 cells loaded with the mutant peptide FMVDGFWSI of the present invention and the wild-type peptide FMVDGSWSI, respectively, into ELISPOTs plates, and cultured for 20 h, and then a ELISPOTs detection was performed (see the kit instruction). Finally, the spots produced by the ELISPOTs detection were counted.

The peptide was determined to have immunogenicity when the number of spots of the tested peptide/the number of spots of an unrelated peptide>2; that is, if the number of spots caused by the tested peptide is more than twice than that of an unrelated peptide, the tested peptide is determined to have immunogenicity.

ELISPOTs detection results of the peptides of the present invention were shown in Table 4 below.

TABLE 4

Secretion of IFN-γ interferon by specific CD8+ T cells stimulated by a peptide

| Peptide and its variants capable of activating T cells | Number of spots in the mutant peptide group | Number of spots in the wild-type peptide group | Fold (tested/wild-type) | Conclusion |
| --- | --- | --- | --- | --- |
| FMVDGFWSI | 332 | 33 | 10.06 | immunogenic |
| FMVDGFWSL | 328 | 37 | 8.86 | immunogenic |
| FMVDGFWSV | 323 | 41 | 7.87 | immunogenic |
| FLVDGFWSI | 314 | 28 | 11.21 | immunogenic |
| FLVDGFWSL | 308 | 30 | 10.26 | immunogenic |
| FLVDGFWSV | 301 | 31 | 9.71 | immunogenic |

It can be seen from Table 4 that the peptide of the present invention and its variants are immunogenic and can specifically activate a CD8+ T cell immune response.

Example 5 Specific Killing Activity of CD8+ T Cells Against Target Cells Presenting the Peptide of the Present Invention as Demonstrated by a LDH Release Assay The cells cultured in Example 3 were co-cultured with T2 cells loaded with the mutant peptides of the present invention or the wild-type peptide or without a peptide. A maximum release well, a volume correction well, a medium control well, a spontaneous release well and control wells for example at different effector-to-target ratios (ratios of T cells to T2 cells) were set in this experiment. Three replicate wells were set for each group. After 4 h, 50 μl of the co-culture supernatant was taken out and added to 50 μl of LDH substrate mixture to catalyze the reaction of LDH substrate. Finally, the plates were read at a wavelength of 490 nm, with a reference wavelength of 680 nm, and the killing activity against target cells T2 was calculated based on the control wells. The test results were shown in FIG. 2 and Table 5 below.

TABLE 5

Specific recognition and killing of target cells presenting test peptides by T cells

| Group | effector-to-target ratio (1:1) | effector-to-target ratio (10:1) |
| --- | --- | --- |
| T cells (FMVDGFWSI) + T2 (FMVDGSWSI) | 2.23% | 5.23% |
| T cells (FMVDGFWSI) + T2 (FMVDGFWSI) | 9.22% | 46.37% |

TABLE 5-continued

Specific recognition and killing of target cells presenting test peptides by T cells

| Group | effector-to-target ratio (1:1) | effector-to-target ratio (10:1) |
| --- | --- | --- |
| T cells (FMVDGFWSL) + T2 (FMVDGSWSI) | 3.12% | 4.91% |
| T cells (FMVDGFWSL) + T2 (FMVDGFWSI) | 9.03% | 44.48% |
| T cells (FMVDGFWSV) + T2 (FMVDGSWSI) | 3.37% | 5.63% |
| T cells (FMVDGFWSV) + T2 (FMVDGFWSI) | 8.76% | 41.36% |
| T cells (FLVDGFWSI) + T2 (FMVDGSWSI) | 2.65% | 5.53% |
| T cells (FLVDGFWSI) + T2 (FMVDGFWSI) | 8.53% | 40.12% |
| T cells (FLVDGFWSL) + T2 (FMVDGSWSI) | 3.13% | 6.33% |
| T cells (FLVDGFWSL) + T2 (FMVDGFWSI) | 8.37% | 37.26% |
| T cells (FLVDGFWSV) + T2 (FMVDGSWSI) | 3.26% | 6.01% |
| T cells (FLVDGFWSV) + T2 (FMVDGFWSI) | 8.07% | 35.24% |

Figure 2:
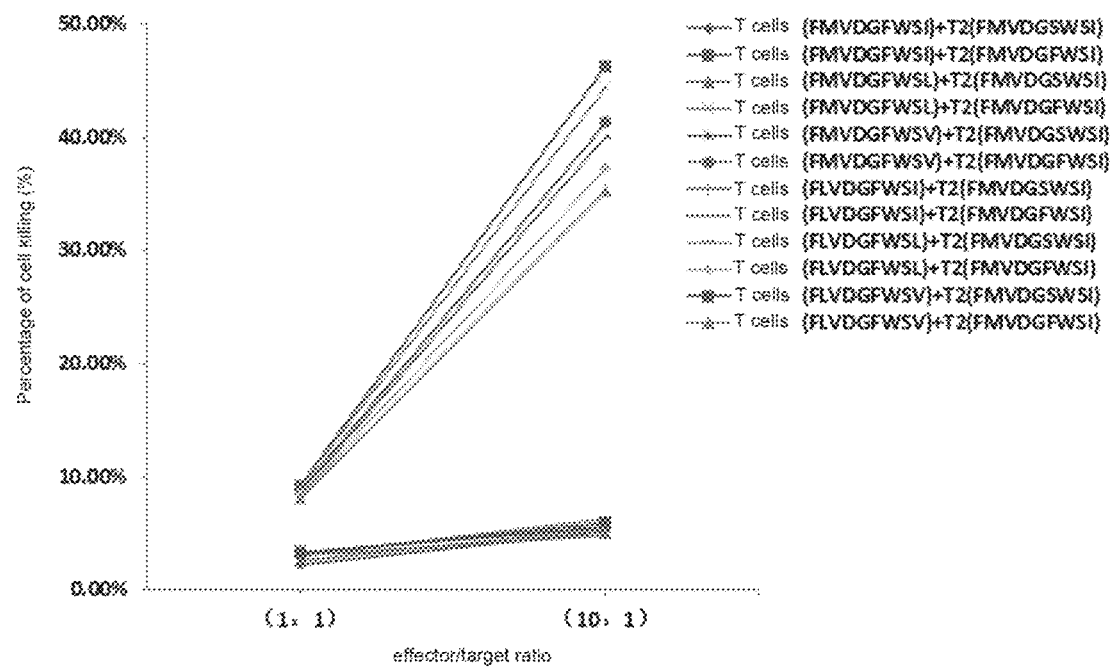
FIG. 2 is a graph showing the results of specific killing of target cells presenting the peptide of the present invention by immune cells.

It can be seen from the results of FIG. 2 and Table 5 that, at an effector-to-target ratio of 1:1 or 1:10, the activated T cells by the mutant peptide FMVDGFWSI of the present invention or the variant peptides thereof were capable of killing T2 cells presenting the mutant peptide, but not the T2 cells presenting a wild-type peptide, further demonstrating that the mutant peptides of the present invention were capable of specifically killing target cells presenting the mutant peptide FMVDGFWSI.

Example 6 Construction and Packaging of Recombinant Lentiviruses of the Mutant Peptide FMVDGFWSI and the Variant Peptides Thereof The following DNA sequences were synthesized: "TTCATGGTGGATGGATCTTGGAGCATA" (SEQ ID NO: 8), encoding the wild-type peptide FMVDGSWSI; "TTCATGGTGGATGGATTCTGGAGCATA" (SEQ ID NO: 9), encoding the mutant peptide FMVDGFWSI; "TTCATGGTGGATGGATTCTGGAGCCTG" (SEQ ID NO: 10), encoding the FMVDGFWSI's variant peptide FMVDGFWSL; "TTCATGGTGGATGGATTCTGGAGCGTC" (SEQ ID NO: 11), encoding the FMVDGFWSI's variant peptide FMVDGFWSV; "TTCCTGGTGGATGGATTCTGGAGCATA" (SEQ ID NO: 12), encoding the FMVDGFWSI's variant peptide FLVDGFWSI; "TTCCTGGTGGATGGATTCTGGAGCCTG" (SEQ ID NO: 13), encoding the FMVDGFWSI's variant peptide FLVDGFWSL; and "TTCCTGGTGGATGGATTCTGGAGCGTC" (SEQ ID NO: 14), encoding the FMVDGFWSI's variant peptide FLVDGFWSV. The wild-type peptide FMVDGSWSI, the mutant peptide FMVDGFWSI and the mutant peptide FMVDGFWSI's variant peptides were constructed into the lentiviral vector pHBLV-Puro, respectively, to name as pHBLV-Puro-FMVDGSWSI, pHBLV-Puro-FMVDGFWSI, pHBLV-Puro-FMVDGFWSL, pHBLV-Puro-FMVDGFWSV, pHBLV-Puro-FLVDGFWSI, pHBLV-Puro-FLVDGFWSL and pHBLV-Puro-FLVDGFWSV, respectively. The seven lentiviral constructs were co-transfected into 293T cells with helper plasmids pSPAX2 and pMD2G for packaging, and lentiviruses of the wild-type peptide FMVDGSWSI, the mutant peptide FMVDGFWSI and the mutant peptide's variant peptides were obtained.

Example 7 Establishment of a Human Lung Cancer Cell Line Expressing the Mutant Peptide FMVDGFWSI The human non-small cell lung adenocarcinoma cell line NCI-H2087 which was HLA-A*0201 positive was purchased from ATCC. The cells were cultured in DMEM medium containing 10% fetal bovine serum, 100 U/mL penicillin and 100 U/ml streptomycin in an incubator at 37° C., 5% $CO_2$. The lentivirus of FMVDGFWSI as packaged in Example 6 was transfected into the H2087 cell line. Transfected cells were continuously screened by using antibiotic puromycin to finally establish a H2087 cell line expressing FMVDGFWSI peptide which was named as H2087-FMVDGFWSI cell line.

Example 8 Human Immune Reconstitution in NOD SCID Mice 600-900 ml of anticoagulated peripheral blood was collected from healthy volunteers for isolating peripheral blood mononuclear cells (PBMCs) via Ficoll. Cells were collected for use. 2×PBMCs per 0.5 ml was intraperitoneally injected into each of 300 NOD SCID mice without immune leakage to perform human immune reconstitution in NOD SCID mice. After 4 weeks, the mice were selected to be inoculated with the human lung cancer cell line.

Example 9 Establishment of a Subcutaneous Xenograft Model of H2087-FMVDGFWSI

The human non-small cell lung adenocarcinoma cell line H2087-FMVDGFWSI as established in Example 7 was cultured in DMEM medium containing 10% fetal bovine serum, 100 U/mL penicillin and 100 U/mL streptomycin in an incubator at 37° C., 5% $CO_2$. H2087-FMVDGFWSI tumor cells were collected, centrifuged at 1500 rpm for 5 min, and washed 3 times with sterile physiological saline. The tumor cells were diluted appropriately. To 40 μl of cell suspension was added 10 μl of 0.4% phenol blue for staining and microscopically counting cells. A tumor cell suspension at a concentration of $1*10^8$ cells/ml was prepared. 100 μl of the tumor cell suspension was inoculated subcutaneously into a NOD/SCID mouse or an immune-reconstituted NOD/SCID mouse. After inoculation, the inoculation site was daily observed for the presence or absence of an infection. It was also observed whether there was a spontaneous regression after tumor growth. The long diameter a and the short diameter b of the tumor were measured with a vernier caliper every 2-3 days and the size of the tumor was calculated as a*b*b/2. The mice and tumors were weighed and recorded every day. After 7 days, a tumor with about the size of a grain of rice could be touched under the skin of mouse. At this time, the H2087-FMVDGFWSI subcutaneous tumor model NOD/SCID mice were treated with DC-CTL vaccines. The H2087-FMVDGFWSI subcutaneous tumor model NOD/SCID mice that had been subjected to immune reconstitution for 4 weeks were treated with a peptide+complete Freund's adjuvant, or a peptide+DC vaccine, or lentivirus-infected DC vaccine, and DC-CTL vaccine, respectively. The tumor volume and the survival rate of mice were recorded every 2 days.

Example 10 Treatment Regimen with Peptide Vaccines

Figure 3:
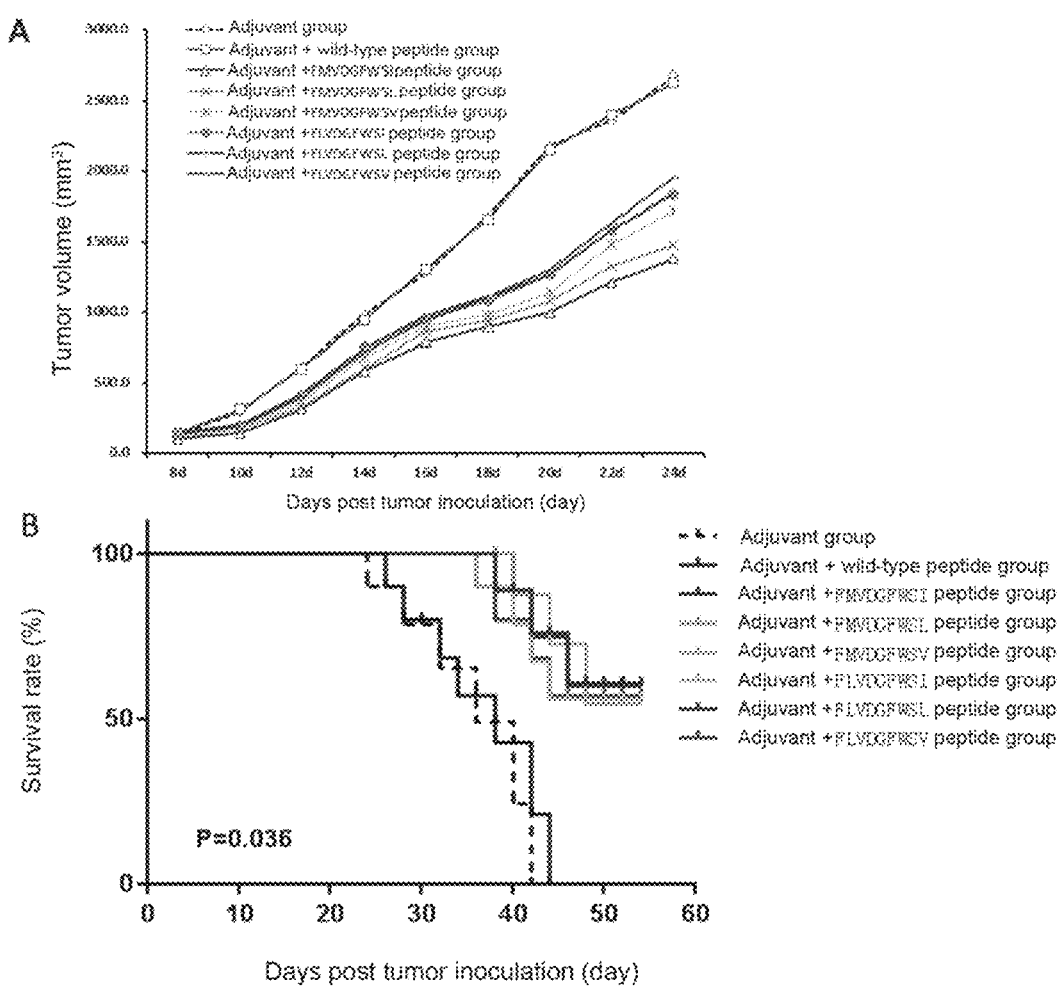

The H2087-FMVDGFWSI subcutaneous tumor model NOD/SCID mice that had been subjected to immune reconstitution for 4 weeks were randomly divided into 8 groups: adjuvant+wild-type peptide group, adjuvant group, adjuvant+FMVDGFWSI peptide group, and groups of adjuvant+ each of the FMVDGFWSI's 5 variant peptides, with 6 mice per group. The first immunization dose of the peptides described above was 100 μg/mouse. Each of the peptides was resuspended in PBS, mixed with 150 μl of Freund's complete adjuvant per mouse, and then adjusted with PBS to 300 μl per mouse, and injected subcutaneously at two points on the back. After 2 weeks, the same dose was used for booster immunization (using a complete Freund's adjuvant for the first one, and using an incomplete Freund's adjuvant for the others), with a total of 4 immunizations. The general characteristics including mental state, activity, response, diet, body weight and tumor growth of the tumor-bearing mice were observed daily. The longest diameter (a) and the shortest diameter (b) of a tumor were measured with a vernier caliper every 2 days. Tumor volume was calculated as: ½×length×width$^2$. The results were shown in FIG. 3. The results showed that, as compared to the adjuvant alone group and the wild-type peptide group, FMVDGFWSI or its variant forms+Freund's adjuvant effectively inhibited tumor growth and prolonged the survival period of mice. The formula for calculating the survival period was as follows: survival rate within a certain period of time=surviving mice within this period of time/(surviving mice within this period of time+dead mice within this period of time)*100%.

Example 11 Preparation of a DC Peptide Vaccine and Treatment Regimen Using this Vaccine 100-150 ml of anticoagulated peripheral blood was collected from healthy volunteers for isolating peripheral blood mononuclear cells via Ficoll. PBMCs were collected, resuspended in RPMI 1640 medium at $2\sim3\times10^6$ cells/ml, and incubated at 37° C. for 2 h. The adherent cells which were DCs were induced into mature DCs with 1000 U/ml GM-CSF, 1000 U/ml IL-4, 100 U/ml IFN-γ and 100 U/ml CD40L. Mature DCs were harvested, and then wild-type peptide, the mutant peptide FMVDGFWSI and the FMVDGFWSI's five variant peptides (at a concentration of 10 μg/ml) were added respectively, co-incubated for 4 hours and then washed with physiological saline for three times. The DCs loaded with a peptide were adjusted to $(4.0\pm0.5)\times10^7$ cells/ml with physiological saline for subsequent experiments.

Figure 4:
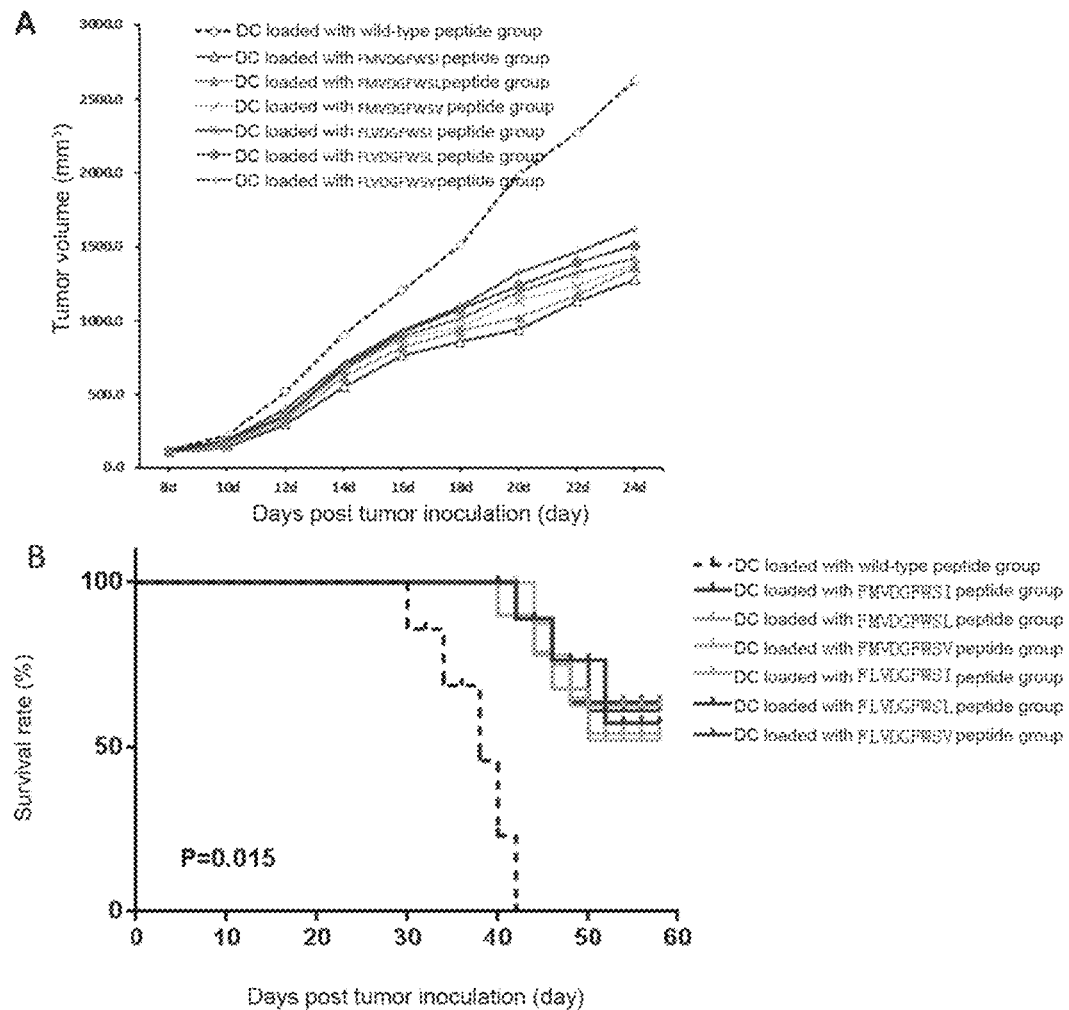

Tumor-bearing mice were randomly divided into 7 groups: DC loaded with wild-type peptide group, DC loaded with the mutant peptide FMVDGFWSI group, and groups of DC loaded with each of the FMVDGFWSI's 5 variant peptides, with 6 mice per group. Cell suspensions of the DCs loaded with wild-type peptide, the DCs loaded with the mutant peptide FMVDGFWSI, and the DCs loaded with each of the FMVDGFWSI's 5 variant peptides were prepared. 0.1 ml was injected intracutaneously into each side of the inner thigh near groin of the tumor-bearing mouse once a week. For each group, the dose was $(4.0\pm0.5)\times10^6$ cells/injection, and a total of 2 injections was performed. After injection, vital signs of the mice were observed, and the vertical and horizontal dimensions of tumors were measured with a vernier caliper every two days. Tumor volume was calculated as follows: tumor volume=½×length×width$^2$. At the same time, the changes in body weight and survival of the mice were recorded. The results were shown in FIG. 4. The results in FIG. 4 showed that, compared to the group of DC vaccine loaded with wild-type peptide, DC vaccines loaded with FMVDGFWSI or the variant peptides thereof significantly prolonged survival period of mice and slowed down tumor growth in mice.

Example 12 Preparation of a DC Vaccine by Injection with Recombinant Lentivirus Containing a Peptide Gene and Treatment Regimen Using this Vaccine 100-150 ml of anticoagulated peripheral blood was collected from healthy volunteers for isolating peripheral blood mononuclear cells via Ficoll. PBMCs were collected, and incubated at 37° C. for 2 h. Non-adherent cells were washed away and DCs were cultured with recombinant human granulocyte-macrophage colony-stimulating factor (rhGM-CSF) and recombinant human interleukin-4 (rhIL-4). On day 5 of culturing, half of the medium was replaced and the cell density was adjusted to $1*10^6$ cell/ml; solutions of recombinant lentiviruses of the wild-type peptide, the mutant peptide FMVDGFWSI or the FMVDGFWSI's five variant peptides (as constructed in Example 6) were added at an appropriate amount. After 24 h, the virus-containing culture medium was removed, and a culture medium containing 50 ng/ml rhIL-4, 100 ng/ml rh GM-CSF, 100 U/ml IFN-γ and 100 U/ml CD40L was added for culturing in an incubator at 37° C., 5% $CO_2$. After 16 h, the DCs were adjusted to $(4.0\pm0.5)\times10^7$ cells/ml for subsequent experiments.

Figure 5:
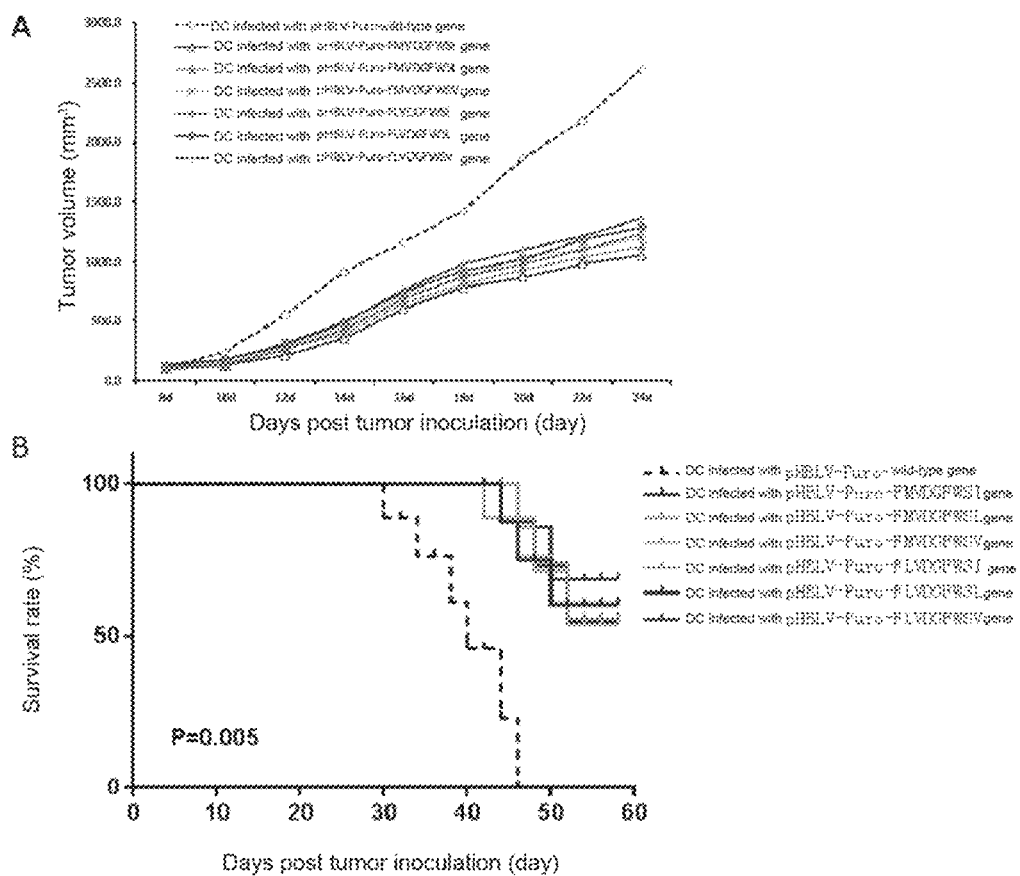

Tumor-bearing mice were randomly divided into 7 groups: wild-type peptide-DC group, FMVDGFWSI peptide-DC group, and groups of each of the FMVDGFWSI's 5 variant peptides-DC, with 6 mice per group. Cell suspensions of the DCs loaded with wild-type peptide, the DCs loaded with the mutant peptide FMVDGFWSI, and the DCs loaded with each of the FMVDGFWSI's 5 variant peptides were prepared. 0.1 ml was injected intracutaneously into each side of the inner thigh near groin of the immune-reconstituted tumor-bearing mouse once a week. For each group, the dose was $(4.0\pm0.5)\times10^6$ cells/injection, and a total of 2 injections was performed. After injection, vital signs of the mice were observed, and the vertical and horizontal dimensions of tumors were measured with a vernier caliper every two days. Tumor volume was calculated as follows: tumor volume=½×length×width². At the same time, the changes in body weight and survival of the mice were recorded. The results were shown in FIG. 5 which showed that the DC vaccines infected with recombinant lentivirus containing gene of the mutant peptide FMVDGFWSI or its five variant peptides had significant tumor-suppressing effects and prolonged the survival period of mice compared to the group of wild-type peptide which had no effect on this tumor.

Example 13 Preparation of a Peptide-Specific CTL Vaccine and a In Vivo Treatment Regimen Using this Vaccine 100-150 ml of anticoagulated peripheral blood was collected from healthy volunteers for isolating peripheral blood mononuclear cells via Ficoll. PBMCs were collected, resuspended in RPMI 1640 medium at $2-3\times10^6$ cells/ml, and incubated at 37° C. for 2 h. The non-adherent cells, which were peripheral blood lymphocytes (PBLs), were pipetted.

The collected PBLs were subjected to magnetic bead sorting to obtain CD8+ T cells, which were sensitized by co-incubation with DCs loaded with the wild-type peptide, DCs loaded with the mutant peptide FMVDGFWSI and its five variant peptides at a cell ratio of DCs:CD8+ T cells=1:4. 500 IU/ml of IL-2 and 50 ng/ml of IL-7 were added to the medium to co-incubate in an incubator at 37° C., 5% $CO_2$, and cell counting was performed after 1 week of culturing; a second round of stimulation was performed at week 2 by adding DCs loaded with FMVDGFWSI peptide, DCs loaded with the FMVDGFWSI's five variant peptides, or DCs loaded with the wild-type peptide, and 500 IU/ml of IL-2. The same procedure was carried out at week 3. Thus, three rounds of stimulation were performed. Medium was appropriately added during culturing. The number of lymphocytes was counted and a cell proliferation index (PI) was calculated on days 0, 7, 14, and 21 of culture, respectively. PI=number of cells after expansion/number of cells inoculated. On day 7 after the third stimulation (i.e., day 21 of culture), cells, i.e., cytotoxic T lymphocytes (CTLs) were harvested. The cells were resuspended in physiological saline to a volume of 0.2 ml, and were reinfused through tail vein at about $1\times10^8$ cells per tumor model mouse. After injection, vital signs of the mice were carefully observed and the vertical and horizontal dimensions of the tumors were measured with a vernier caliper every 2 days.

Figure 6:
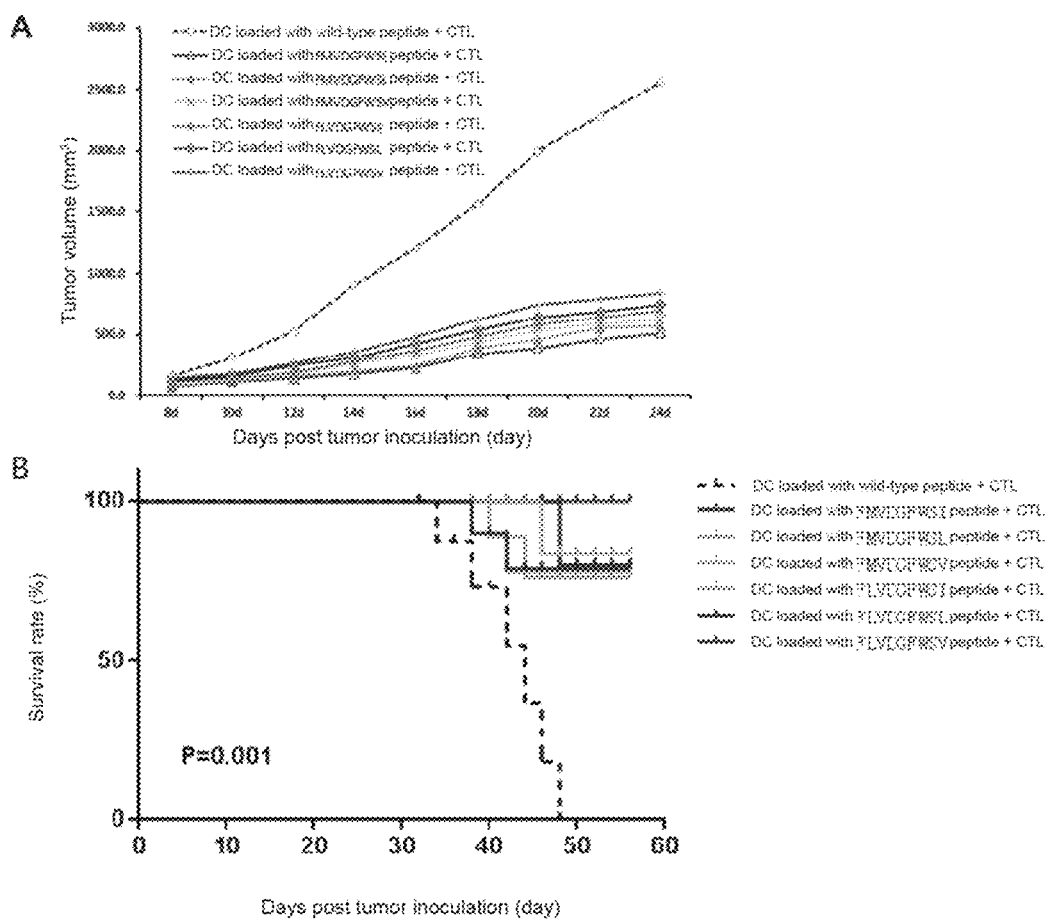

The results were shown in FIG. 6. The results in FIG. 6 showed that, compared to the wild-type peptide group, the DC-CTL vaccines that were activated by the mutant peptide FMVDGFWSI or the five variant peptides thereof had significant tumor-suppressing effects and prolonged the survival period of mice.

The Applicant states that the method of the present invention and application and effects thereof are illustrated through the above examples, however, the present invention is not limited thereto. Those skilled in the art should understand that, for any improvement of the present invention, the equivalent replacement of the products of the present invention, the addition of auxiliary components, and the selection of specific modes, etc., will all fall within the scope of protection and the scope of disclosure of the present invention.

---

The invention claimed is:

1. An isolated peptide, wherein the peptide is selected from the group consisting of:
   (a) a peptide consisting of the amino acid sequence shown in SEQ ID NO: 2; and
   (b) a peptide which is derived from the amino acid sequence shown in SEQ ID NO: 2 by substitution of an amino acid residue at position 2 and/or substitution of an amino acid residue at position 9, and has the ability to induce cytotoxic T lymphocytes.

2. The peptide according to claim 1, wherein the peptide can be recognized by CD8+T cells.

3. The peptide according to claim 1, wherein the peptide in (b) is derived from the amino acid sequence shown in SEQ ID NO: 2 by substitution of the amino acid at position 2 with L and/or substitution of the amino acid at position 9 with L or V.

4. The peptide according to claim 3, wherein the peptide in (b) has the amino acid sequence as shown in SEQ ID NO: 3, SEQ ID NO: 4, SEQ ID NO: 5, SEQ ID NO: 6, or SEQ ID NO: 7.

5. An isolated nucleic acid encoding the peptide according to claim 1.

6. A vaccine for treating a tumor expressing the peptide corresponding to SEQ ID NO: 2 and HLA-A0201 in a patient, comprising the peptide according to claim 1.

7. The vaccine according to claim 6, wherein the tumor is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

8. A therapeutic method for treating a patient having a tumor expressing the peptide corresponding to SEQ ID NO:2 and HLA-A0201, comprising:
   administering to the patient an effective amount of the peptide according to claim 1.

* * * * *